US00PP07979P

United States Patent [19]

Twomey

[11] Patent Number: Plant 7,979

[45] Date of Patent: Sep. 22, 1992

[54] GRANDIFLORA ROSE PLANT NAMED TWOLOY

[75] Inventor: Jerry Twomey, Leucadia, Calif.

[73] Assignee: DeVor Nurseries, Inc., Watsonville, Calif.

[21] Appl. No.: 641,003

[22] Filed: Jan. 11, 1991

[51] Int. Cl.[5] ..... A01H 5/00

[52] U.S. Cl. ..... Plt./11

[58] Field of Search ..... Plt./11, 12, 18, 19, Plt./20, 22, 26, 27, 28

*Primary Examiner*—Howard J. Locker

*Attorney, Agent, or Firm*—Christie, Parker & Hale

[57] ABSTRACT

A new grandiflora rose plant producing pink flowers.

1 Drawing Sheet

SUMMARY OF THE INVENTION

The present invention relates to a new and distinct variety of rose plant of the grandiflora rose class which was originated by my crossing as seed parent the variety known as 'Brion' and as pollen parent an unnamed and unpatented seedling of my creation. The varietal denomination of this new rose is 'Twoloy'.

Among the novel characteristics possessed by this new variety which distinguished it from its parents and all other varieties of which I am aware are its clusters of pink flowers borne on a plant particularly suitable for use in gardens. Flowers open well and are long lasting on the plant and after cutting. The new variety is also characterized by its health, vigor and flower production.

Asexual reproduction by budding and rooting of cuttings of the new variety as performed in Glenn County, Calif. and Kern County, Calif., shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

'Twoloy' is an unusually fine grandiflora rose of pink flower coloration. It is especially well suited for growing outdoor in gardens. The new variety blooms freely and continuously under natural growing conditions on a tall, upright plant in clusters of up to twelve large blooms. 'Twoloy' also does well on its own roots.

The following is a detailed description on my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—'Brion'.

*Pollen parent.*—Unnamed seedling.

Class: Grandiflora.

The following information is from observations made of specimens grown outdoors in Watsonville, Calif.

FLOWERS

Blooming Habit: Continuous, profuse.

A. Bud:

(1) *Size.*—Medium; about 2.5 cm in diameter and 3.5 to 4 cm in length.

(2) *Form.*—Medium, pointed, slow opening.

(3) *Color.*—As sepals divide, bud color is near 51A to 47A.

(4) *Sepals.*—5 in number; simple to foliaceous. Color: Inside — near 192B with near 146C hairs covering surface. Outside — near 143A with near 166A.

(5) *Peduncle.*—Length: 7 cm to 7.5 cm. Aspect: Straight with small prickles. Strength: Erect, rigid. Color: Near 183A with tinges of near 146B.

(6) *Calyx.*—Shape: Funnel shaped; does not split; smooth. Size: Medium; 1.3 cm×1.1 cm.

Bloom:

(1) *Size.*—Large, average size when fully expanded — about 12 to 13 cm; depth about 5 to 5.5 cm.

(2) *Borne.*—Clusters of up to 12 blooms.

(3) *Form.*—Cupped, slightly high centered.

(4) *Petalage.*—Number of petals under normal conditions — about 23 to 25.

(5) *Color.*—After sepals fall and petals unfurl, predominant bud color is near 51A. Flower color viewing petals' top surface is near 51A to 51C with deeper tones where petals bunch and lighter tones on outer petals. Undersurface of petals is light pink near 51D to 58D at perimeter of petals and near white/light pink at centers. Individual petal top surface is near 73D. Color is general and substantially constant. Color at point of petal attachment is near 9A.

C. Petals:

(1) *Texture.*—Medium.

(2) *Appearance.*—Inside velvety and outside satiny.

(3) *Form.*—Round, slightly lobed, notched at apex.

(4) *Arrangement.*—Regularly arranged, imbricated.

(5) *Fragrance.*—Mild, fruity.

(6) *Lasting Quality.*—Long lasting on plant and as cut flower.

REPRODUCTIVE ORGANS

A. Stamens:

*Number.*—Approximately 161 to 165.

*Arrangement.*—Mostly introrse.
*Anthers.*—Size — 0.3 to 0.4 cm. Color — near 15D.
*Filaments.*—(Threads): Length — 0.5 to 0.9 cm. Color — near 23B.
*Pollen.*—Color — near 20A.

Pistils:
*Number.*—Approximately 147 to 150.
*Styles.*—Length — 1 to 1.3 cm. Color — near 51B near tip with near 2D on remainder.
*Stigmas.*—Color — near 11A.

C. Characteristics of ovaries: Small, rounded and slightly flattened, with silvery hairs.

D. Hips:
*Fertile.*—Yes.
*Shape.*—Round.
*Color at maturity.*—Near 169B; 2.4 cm×2.3 cm.

PLANT

A. Form: Upright.

B. Growth: Vigorous, upright; free branching; height attained about 170 to 180 cm at three years.

C. Foliage: Compound 3, 5 and 7 leaflets.
(1) *Size.*—About 16 cm×14 cm.
(2) *Quantity.*—Abundant.
(3) *Color.*—Upper side — near 147A. Under side — near 147B.
(4) *Shape.*—Oval, pointed.
(5) *Texture.*—Semi-leathery; upper side is semi-glossy, under side is matte.
(6) *Edge.*—Serrate, (denticulate).
(7) *Serration.*—Ordinary.

(8) *Leaf stem.*—Color — medium green.
(9) *Stipules.*—Hairy, adnate with some glands.
(10) *Petiolule.*—About 0.5 cm.
(11) *Rachis.*—About 5.5 cm on 3 leaf; 7 cm on 5 leaf; 10 cm on 7 leaf.
(12) *Petioles.*—Length — 1 to 2 cm on 3 leaf; 2 cm on 5 leaf; 2.5 cm on 7 leaf.
(13) *Ribs and veins.*—Both slightly depressed on top and slightly rounded underneath. Rachis: Small spines underneath.
(14) *Resistance to disease.*—Moderately resistant to mildew, rust and black spot.

D. Wood:
(1) *New wood.*—Color — purple/red. Bark — smooth.
(2) *Old wood.*—Color — purple/red. Bark — smooth.

E. Thorns:
(1) *Thorns.*—Quantity (main stalk) — average. On laterals from stalk — average. Form — thin straight, angled downward. Length — 0.8 to 1.3 cm. Color — near 165B. Position — irregular.
(2) *Prickles.*—Few to none present.

F. Winter hardiness: Needs protection in severe climates.

I claim:

1. A new and distinct variety of rose plant of the grandiflora rose class, substantially as shown and described.

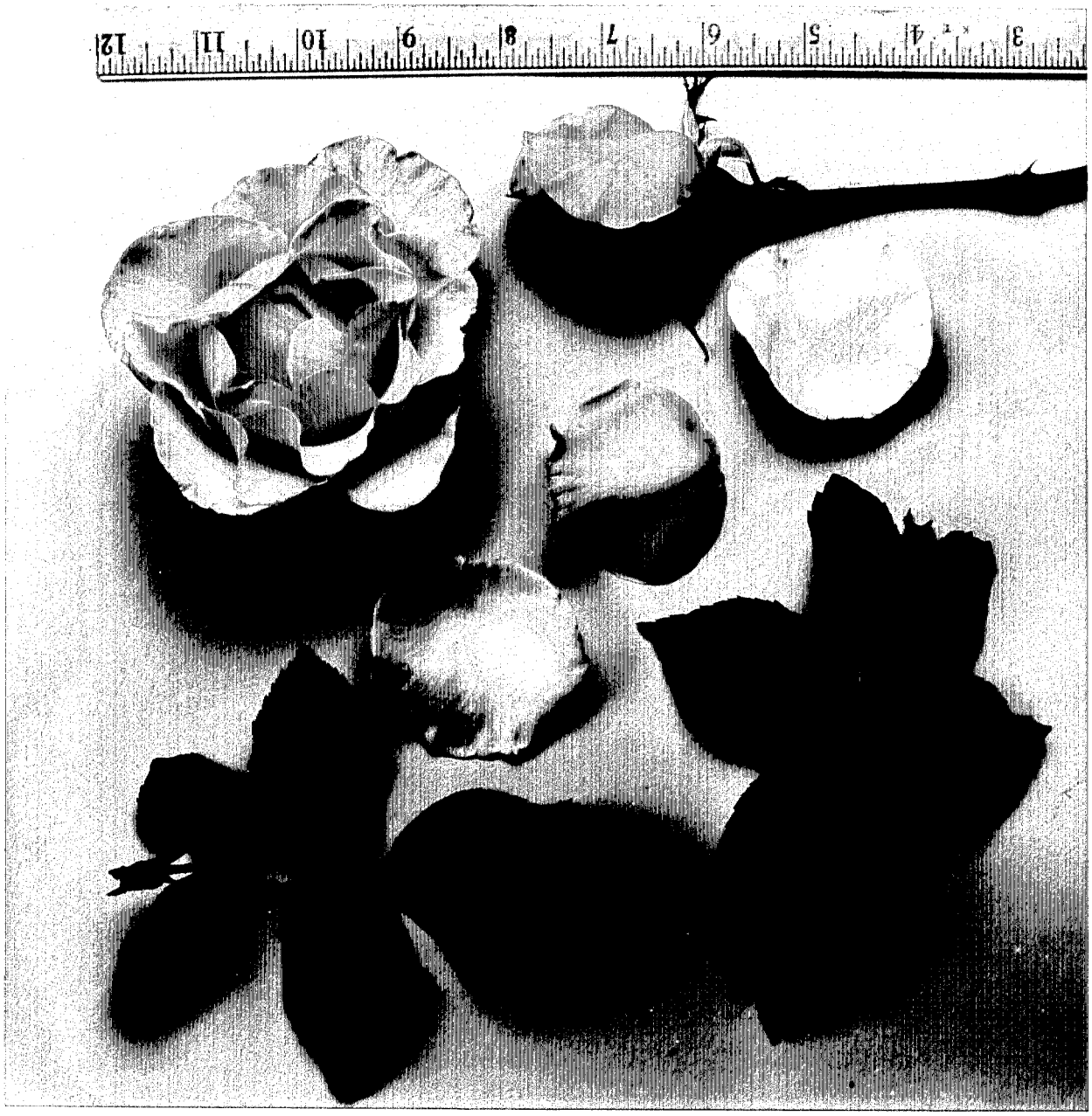

* * * * *